United States Patent [19]

Delcommune et al.

[11] Patent Number: 5,007,939

[45] Date of Patent: Apr. 16, 1991

[54] ARTICLE MADE OF LACTIC ACID POLYMER CAPABLE OF BEING EMPLOYED PARTICULARLY AS A BIODEGRADABLE PROSTHESIS AND PROCESS FOR ITS MANUFACTURE

[75] Inventors: Luc Delcommune, Monfalcone, Italy; Philippe Ghyselinck, Braine-L'Alleud, Belgium

[73] Assignee: Solvay & Cie (Societe Anonyme), Brussels, Belgium

[21] Appl. No.: 269,879

[22] Filed: Nov. 7, 1988

[30] Foreign Application Priority Data

Nov. 19, 1987 [FR] France .................. 87 16147

[51] Int. Cl.$^5$ .......................... A61F 2/02; A61F 2/28; A61B 17/56
[52] U.S. Cl. .................................. 623/66; 623/16; 623/11; 606/77
[58] Field of Search ............... 128/335.5; 623/16, 66; 525/410, 415; 528/354; 606/77

[56] References Cited

U.S. PATENT DOCUMENTS 3,636,956  1/1972  Schneider .................. 128/335.5
4,898,186  2/1990  Ikada et al. ................. 623/16 X

FOREIGN PATENT DOCUMENTS 0133355  2/1985  European Pat. Off. .
0146398  6/1985  European Pat. Off. .
0157601  10/1985 European Pat. Off. .
1478695  4/1967  France .
2088548  1/1972  France .
2156513  6/1973  France .
1123445  8/1968  United Kingdom .

OTHER PUBLICATIONS

"Biomaterials" 190, pp. 271–280.
"Orthopaedic Review" vol. X, No. 11, Nov. 1981; pp. 41–51.

*Primary Examiner*—Alan W. Cannon
*Attorney, Agent, or Firm*—Spencer & Frank

[57] ABSTRACT

Article made of lactic acid polymer capable of being employed particulaly as a biodegradable prosthesis exhibiting at 23° C. a tensile regidity modulus higher than 5000 MPa and a tensile resilience higher than 500 kJ/m$^2$ and a heat shrinkage of less than 50% at 130° C.

The article is produced by forging a blank at a temperature of between 80° and 170° C., with a draw ratio of 200 to 1000%.

9 Claims, No Drawings

ARTICLE MADE OF LACTIC ACID POLYMER CAPABLE OF BEING EMPLOYED PARTICULARLY AS A BIODEGRADABLE PROSTHESIS AND PROCESS FOR ITS MANUFACTURE

The present invention relates chiefly to an article made of lactic acid polymer capable of being employed particularly as a biodegradable prosthesis, in particular in bone surgery, and exhibiting improved mechanical properties.

A biodegradable prosthesis needs to meet two requirements; on the one hand, it must be sufficiently rigid for the knitting of the fractured bony parts to be able to take place at the beginning of the cure and, on the other hand, it must be sufficiently flexible to promote the formation of a bony callus by means of the stresses applied to the members.

Lactic acid polymers, and in particular the homopolymer of L-lactic acid, which have already been envisaged for the production of such prostheses have been judged too rigid and especially too brittle (Biomaterials, 1980,3, p.276). In order to overcome these mechanical shortcomings, it was then proposed to reinforce this material with fibres such as carbon fibres (Orthoped. Rev. 1981,10, p.41), polyglycolic acid (Biomaterials 1980, p.271) or else calcium metaphosphate (European Patent application No. 0,146,398). To be sure, by proceeding in this manner, it is possible to produce prostheses having an acceptable stiffness, but it is found that they remain fragile. Moreover, it is quite obvious that the production of such prostheses is tricky and costly.

The Applicant Company has now found that it is possible to produce directly from a lactic acid polymer articles such as biodegradable prostheses which have remarkable mechanical characteristics, making them particularly effective, especially in bone surgery.

The present invention consequently relates to an article made of lactic acid polymer capable of being employed particularly as a biodegradable prosthesis exhibiting at 23° C. a tensile rigidity modulus higher than 5000 MPa and, preferably, higher than 7500 MPa and a tensile resilience higher than 500 kJ/m$^2$, and, preferably, higher than 3000. In a preferred embodiment, the article in accordance with the invention exhibits, furthermore, a heat shrinkage of less than 15% at 130° C.

The lactic acid polymers employed for producing the articles according to the invention are chosen from thermoplastic polymers resulting from the homopolymerization of L-lactic acid, from the copolymerization of L-lactic acid and D-lactic acid in a proportion of 99 to 50% of L-lactic and/or with other copolymerizable monomers. These other copolymerizable monomers may be, for example, beta-propiolactide, tetramethylglycolide, beta-butyrolactone, gamma-butyrolactone, pivalolactone, alpha-hydroxyacetic acid, alpha-hydroxybutyric acid, alpha-hydroxyisobutyric acid, alpha-hydroxyvaleric acid, alpha-hydroxyisovaleric acid, alpha-hydroxycaproic acid, alpha-hydroxyisocaproic acid, alpha-hydroxy-alpha-ethylbutyric acid, alpha-hydroxy-heptanoic acid, alpha-hydroxystearic acid and the like.

The resultant copolymers may be either random copolymers or so-called "block" copolymers. These block copolymers consist of a series of chain segments of various length, each segment consisting of a homopolymer of a monomer or of a random copolymer comprising two or more comonomers such as defined above.

The preferred biodegradable polymers for the production of prostheses according to the invention are homopolymers of L-lactic acid and copolymers of L-lactic acid and of D-lactic acid containing from 99 to 50% of L-lactic acid. Resulting to a copolymer of L-lactic acid and of D-lactic acid offers the advantage of permitting the biodegradation period to be controlled by modifying the content of units derived from D-lactic acid.

For reasons of retention of mechanical properties of the prostheses with time, polymers of lactic acid which are particularly suitable for the invention are those whose average molecular weight is greater than 250,000 and, preferably, than 400,000. This average molecular weight is defined by the relationship $M_w = \Sigma\, ni\, Mi^2 / \Sigma\, ni\, Mi$ in which ni denotes the number of molecules of molecular weight Mi. This average molecular weight is determined in a known manner by means of cryoscopic and ebullioscopic methods, by the end group method or by osmometry.

The article in accordance with the invention may be produced in particular by extruding a blank made of lactic acid polymer at 170°-250° C., by heat-aging the blank at a temperature of 80°-170° C., and then by subjecting it to a drawing to 200-1000%. Advantageously, the article can be finally annealed under tension at a temperature of at least 130° C.

The blank may be produced by conventional fabrication techniques, generally extrusion or injection. However, it is possible to employ other techniques such as, for example, sintering. The blank may be of any cross-section: circular, oval, polygonal and the like. The blank is preferably in the form of a cylinder or of a small plate.

The temperature for aging the blank before it is drawn lies 10° to 100° C. below the melting temperature of the material, that is at a temperature of 80° to 170° C. The aging may be carried out in an oven or in the barrel of an extruder from which the screw has been withdrawn. The aging time of the blank must be at least equal to the time needed for the temperature to become uniform throughout the mass of the material. Materials which are readily oxidizable when heated must be protected with an inert gas such as, for example, nitrogen. The aging period is generally between 5 and 120 minutes and, preferably, between 15 and 90 minutes.

The blank aged in this manner is then subjected to an axial drawing as described previously. In a preferred embodiment, the heat aging is carried out in the barrel of an extruder, as mentioned before, and the drawing stage is performed by drawing the blank through a convergent die fitted to the extruder, the exit section corresponding to that desired in the case of the article to be produced. The relationship between the initial section of the blank and the exit section of the convergent die gives the draw ratio applied to the blank. This ratio is preferably from 200 to 1000%. The rate of drawing is between 50 and 1000 mm/min and, preferably, between 100 and 500 mm/min. Like all molecular orientation processes, the drawing of the blank according to the embodiment thus described results in causing internal stresses to appear in the constituent material. When the biodegrable prosthesis thus produced is required to be subsequently sterilized at a temperature close to or above the drawing temperature, it is preferable to subject the article to an additional heat stabilization stage, because the temperature limit for the use of an article without preliminary stabilization lies approximately 20° to 40° C. below the drawing temperature. Depending on the size of the articles, a satisfactory stabilization may be obtained by an annealing for 30 to 90 minutes at a temperature 5° to 20° C. above the temperature for sterilising the biodegradable prostheses.

In certain cases, the stabilization may also be employed to obtain close tolerance limits by carrying out a check on the dimensions during the stabilization. Thus, for example, the outer diameter of a cylindrical article may be determined accurately by threading a calibrated tube around the article during the stabilization.

Although the articles according to the invention may be produced in various forms, the cylindrical shape has been chosen in the examples which will follow, this shape being particularly suitable for biodegradable prostheses which need to be implanted inside fractured bony parts.

The examples which follow serve to illustrate the invention.

EXAMPLE 1

A laboratory single-screw extruder fitted with a tubular die 17.2 mm in diameter is fed with a homopolymer of L-lactic acid of average molecular weight of 500,000 and whose melting temperature is 172° C., the temperatures applied in the various extruder zones being the following:
165° C. in the feed zone
180° C. in the compression zone
180° C. in the metering zone
180° C. in the case of the exit die.

The liquid cylindrical rod leaving the extruder has a diameter of 16.5 mm after cooling and solidifying.

The rod is then heat-aged in the barrel of an extruder without a screw and fitted with a convergent round die with an exit diameter of 6 mm. The temperature for aging the rod is fixed at 150° C. and the aging period at 60 minutes. The aged rod is then drawn through the convergent exit die at a draw rate of 200 mm/min. The diameter of the drawn rod thus produced is 5.5 mm which corresponds to a draw ratio of 9. The drawn rod is then annealed for 60 minutes at 130° C. under tension.

The mechanical properties of the article thus obtained, measured according to ISO Standard 527 give the following results:

| | |
|---|---|
| tensile elasticity modulus | = 8830 MPa |
| breaking stress | = 176 MPa |
| elongation at break | = 11% |
| maximum elastic stress | = 182 MPa |
| elongation at the maximum elastic stress | = 8%. |

The tensile resilience, measured according to DIN Standard 53448 is 3600 kJ/m².

EXAMPLE 1R

This example is given by way of comparison.

The 16.5-mm diameter cylindrical rod obtained in Example 1 is pressed at 195° C. to form a plate 2 mm in thickness and is then cooled and solidified.

The mechanical properties, measured according to ISO Standard 527, give the following results:

| | |
|---|---|
| tensile elasticity modulus | = 3670 MPa |
| maximum elastic stress | = 66 MPa |
| elongation at the maximum elastic stress | = 2.4% |
| breaking stress | = 59 MPa |
| elongation at break | = 3.6%. |

The tensile resilience, measured according to DIN Standard 53448 is 94 kJ/m². The plaque thus obtained is characterized by a great fragility, which makes it unsuitable for use as a prosthesis in bone surgery.

We claim:

1. A biodegradable prosthesis comprising a molecularly oriented lactic acid polymer exhibiting at 23° C. a tensile rigidity modulus higher than 5000 MPa and a tensile resilience higher than 500 kJ/m².

2. The biodegradable prosthesis according to claim 1, wherein said molecularly oriented lactic acid polymer additionally exhibits a heat shrinkage of less than 15% at 130° C.

3. The biodegradable prosthesis according to claim 1, wherein said molecularly oriented lactic acid polymer is a homopolymer of L-lactic acid.

4. The biodegradable prosthesis according to claim 1, wherein said molecularly oriented lactic acid polymer has an average molecular weight greater than 250,000.

5. The biodegradable prosthesis according to claim 1, wherein said molecularly oriented lactic acid polymer has an average molecular weight greater than 400,000.

6. The biodegradable prosthesis according to claim 1, wherein said molecularly oriented lactic acid polymer exhibits at 23° C. a tensile rigidity modulus higher than 7,500 MPa.

7. The biodegradable prosthesis according to claim 1, wherein said molecularly oriented lactic acid polymer exhibits a tensile resilience higher than 3,000 kJ/m².

8. The biodegradable prosthesis according to claim 1, wherein said molecularly oriented lactic acid polymer is produced by extruding a blank made of lactic acid polymer at a temperature between about 170° and 250° C., heat-aging the extruded blank at a temperature between about 80° and 170° C., and then drawing the aged blank to between about 200 and 1,000%.

9. The biodegradable prosthesis according to claim 8, wherein said molecularly oriented lactic acid polymer is annealed under tension at a temperature of at least about 130° C.

* * * * *